US007968518B2

(12) United States Patent
Hijikata et al.

(10) Patent No.: US 7,968,518 B2
(45) Date of Patent: Jun. 28, 2011

(54) USE OF MODIFIED CYCLOSPORINS FOR THE TREATMENT OF HCV DISORDERS

(75) Inventors: Makoto Hijikata, Kyoto (JP); Kunitada Shimotohno, Kyoto (JP); Koichi Watashi, Kyoto (JP)

(73) Assignee: Novartis AG, Basel (CH)

( * ) Notice: Subject to any disclaimer, the term of this patent is extended or adjusted under 35 U.S.C. 154(b) by 914 days.

(21) Appl. No.: 10/570,097

(22) PCT Filed: Sep. 2, 2004

(86) PCT No.: PCT/EP2004/009804
§ 371 (c)(1),
(2), (4) Date: Dec. 7, 2006

(87) PCT Pub. No.: WO2005/021028
PCT Pub. Date: Mar. 10, 2005

(65) Prior Publication Data
US 2007/0275884 A1    Nov. 29, 2007

(30) Foreign Application Priority Data
Sep. 3, 2003  (GB) ................................. 0320638.0

(51) Int. Cl.
*A61K 38/12*    (2006.01)
*A61K 39/29*    (2006.01)
*A61K 38/13*    (2006.01)

(52) U.S. Cl. .................... 514/20.5; 530/317; 424/149.1; 514/21.1

(58) Field of Classification Search ........................ None
See application file for complete search history.

(56) References Cited

U.S. PATENT DOCUMENTS

| 5,994,299 | A | 11/1999 | Carry et al. |
| 6,524,570 | B1 | 2/2003 | Glue et al. |
| 6,927,208 | B1 * | 8/2005 | Wenger et al. ............... 514/9 |
| 2002/0013272 | A1 * | 1/2002 | Cavanak et al. ............. 514/11 |
| 2002/0102279 | A1 | 8/2002 | Chiba et al. |
| 2003/0213603 | A1 | 11/2003 | Ambuhl et al. |

FOREIGN PATENT DOCUMENTS

| EP | 0 484 281 | 5/1992 |
| EP | 1 633 287 B1 | 7/2009 |
| WO | 99/62540 | 12/1999 |
| WO | 02/32447 | 4/2002 |
| WO | 2004/002422 | 1/2004 |
| WO | 2005/021028 | 3/2005 |
| WO | 2006/038088 | 4/2006 |
| WO | 2006/071619 | 7/2006 |

OTHER PUBLICATIONS

Inoue, et al., 2003, J. Gastroenterology, 38, 567-572.*
Watashi, et al., 2003, Hepatology, 38, 1282-1288.*
[Retrieved from]: http://www3.niaid.nih.gov/topics/hepatitis/hepatitisC/prevention.html, 2009, 2 pages [Retrieved on Jun. 27, 2009].*
Hansson, 2004, Journal of Bioenergetics and Biomembranes, 36, 407-413.*
Inoue, 2003, J Gastroenterol, 38, 567-572.*
Papageorgiou, 1996, Bioorganic and Medicinal Chemistry Letters, 6, 23-26.*
Steinkasserer, 1995, Journal of Virology, 69, 814-824.*
Inoue, 2001, Nippon Rinsho (translation enclosed) (referred further as 'Inoue (Nippon)'), in view of Bouchard, 2003, Journal of Virology, 77, 7713-7719 in view of Bartz, 1995, PNAS, 92, 5381-5385.*
Bouchard, 2003, Journal of Virology, 77, 7713-7719.*
Bartz, 1995, PNAS, 92, 5381-5385.*
Inoue, 2001, Nippon Rinsho copy of translation enclosed furnished earlier.*
Kakuma, J. of Gastroenterology and Hepatology, 1997, 12, 62-66.*
Inoue et al. "Hepatitis C. virus and cyclosporin A", Igaku no Ayumi, 193(12), pp. 951-954 (2000) Included are copies of the English abstract, the original doucment in Japanese, and an English translation of the original Japanese document.
Inoue et al. "Antiviral effect of cyclosporin A", Antiviral Development and Therapy Poster Presentation, National Institutes of Health, Jun. 6-9, 1999.
Yoshiba et al. "Interferon and cyclosporin A in the treatment of fulminant viral hepatitis", Journal of Gastroenterology, 30:67-73 (1995).
Steinkasserer et al. "Mode of action of SDZ NIUM 811, a nonimmunosupressive cyclosporin A analog with activity against human immunodeficiency virus type 1 (HIV-1): interference with early and late events in HIV-1 replication", Journal of Virology, vol. 69, 814-824 (Feb. 1995).
Watashi, et al. "Cyclosporin A suppresses replication of hepatitis C virus genome in cultured hepatocytes", Hepatology vol. 38, No. 5 1282-1288 (2003).
Billich A et al. "Mode of Action of SDZ NIM 811, a Nonimmunosuppressive Cyclosporin A analog with Activity against Human Immunodeficiency Virus (HIV) Type 1: Interference with HIV Protein-Cyclophilin A Interactions", Journal of Virology, vol. 69, No. 4, pp. 2451-2461 (1995).
Watashi, K. et al., "Cyclosporin A supresses Replication of Hepatitis C Virus Genome . . . ", Williams and Wilkins, Baltimore, MD, US, 2003, Hepatology, vol. 38, No. 5, pp. 1282-1288.
Retrieved from: http://www3.niad.nih.gov/topics/hepatitisC/prevention.html, 2009, 2 pages [Retrieved on Jun. 27, 2009].
International Search Report, Mar. 6, 2006.
Renken, J., Observations under Article 115 EPC, Hoffmann Eitle, Jun. 22, 2007, pp. 2-7.
U.S. Appl. No. 11/572,110, filed Jan. 11, 2008, Cornu-Artis, C., et al.
U.S. Appl. No. 11/720,105, filed May 24, 2007, Kai Lin , W. et al.
U.S. Appl. No. 11/719,684, filed Jan. 29, 2009, Weidmann ,B.
U.S. Appl. No. 12/444,941, filed Apr. 9, 2009, Kohjima M. et al.
EPO, Third Party Observations Under Article 115 EPC, EP 04 764 762.3 (WO 2005/021028) Novartis, Feb. 19, 2007, pp. 1-4.
EPO, Observations by third party pursuant to Art. 115 EPC, Art. 54 EPC, ART 123(2) EPC, Art. 83 EPC, Art 84 EP, Feb. 8, 2007, pp. 1-6.
Evers et al., "Synthesis of Non-immunosuppressive Cyclophilin-Binding . . . ", Bioorganic & Medicinal Chemistry Letters, 2003, vol. 13, pp. 4415-4419.

(Continued)

*Primary Examiner* — Andrew D Kosar
*Assistant Examiner* — Satyanarayana R Gudibande
(74) *Attorney, Agent, or Firm* — Leslie Fischer; Regina Bautista

(57) ABSTRACT

Disclosed are non-immunosuppressive cyclophilin-binding cyclosporins, e.g., of formula (I, Ia or II) as defined herein, having useful properties in the prevention of Hepatitis C infections.

13 Claims, 2 Drawing Sheets

OTHER PUBLICATIONS

Fukushima et al., "Fasudil hydrochloride hydrate, a rhokinase (ROCK) inhibitor, suppresses collagen production and enhances collagenase activity in hepatic stellate cells", 2005, Liver International, vol. 25, pp. 829-838.

Fukushima et al., "Hydroxyfasudil, a Rho-kinase (ROCK) inhibitor suppresses cell growth and collagen production in rat hepatic stellate cells", 2003, Hepatology, vol. 38, No. 4, Suppl. 1, p. 562A.

Nakamuta et al., "Cyclosporine suppresses cell growth and collagen production in hepatic stellate cells", 2005, Transplantation Proceedings, vol. 37, No. 10.

Kozlowski et al., ,Development of pegylated interferons for the treatment of chronic hepatitis C, BioDrugs, vol. 15, No. 7, pp. 419-429 (2001).

Inoue et al., "Combined interferon A2b and cyclosporine A in the treatment of chronic hepatitis C: controlled trial", Journal of Gastroenterol, vol. 38, No. 6, pp. 567-572, , Jun. 2003.

Agid et al., "MR diffusion-weighted imaging in a case of West Nile virus encephalitis", Dec. 23, 2003, Neurology, vol. 61., No. 12, pp. 1821-1823.

Ravindra, K. V. et al., "West Nile virus-associated encephalitis in recipients of renal and pancreas transplants . . . ", May 1, 2004, Clinical Infectious Diseases, vol. 38, No. 9, pp. 1257-1260.

Quesniaux, V. F. J. et al., "Cyclophilin binds to the region of cyclosporine involved in its immunosuppressive . . . ", 1987, European Journal of Immunology, vol. 17, No. 9, pp. 1359-1365.

Papatheodoridis and Cholongitas (2003), J. Viral Hep., 11:287-296.

Watashi, Koichi et al. "Current approaches for developing new anti-HCV agents and analyses of HCV replication using anti-HCV agents", Biosis, Biosciences Information Service , Philadelphia, PA, US; vol. 55, No. 1, pp. 105-110, Jun. 2005.

Duncan and Youossi (2003), Cleveland Clinic, J. Med., 70:S21-S26.

Tripi et al., "Interferon-alpha Alone versus interferon-alpha plus Ribavirin in Patients with Chronic Hepatitis C Not Responding to Pervious Interferon-alpha treatment.", BioDrugs, vol. 13, No. 4, pp. 229-304 (Apr. 2000) (Abstract).

Brown et. al., "Liver Transportation", Current opinion gastroenterology, vol. 17, No. 3, pp. 299-303 (May 2001).

Ferenci, P., International Journal Of Clinical Practice, vol. 57, No. 7, pp. 610-615, "Peginterferon alfa-2a (40KD) (Pegasys) for the treatment of patients with chronic hepatitis C", Sep. 7, 2003.

Manns, M.P., et al., The Lancet, vol. 358, No. 9286, pp. 958-965, "Peginterferon alfa-2b plus ribavirin compared with interferon alfa-2b plus ribavirin for initial treatment of chronic hepatitis C: a randomised trial", Aug. 2001.

Manzarbeitia, C., et al., "40 kDa Peginterferon alfa-2A (PEGASYSs®) as a prophylaxis agent hepatitis C infection recurrence after liver transplantation (LT): preliminary results of a randomized multicenter trial", p. 406A, AbstractsAASLD No. 938, Oct. 2001.

Nakagawa, M., et al., Biochemical and Biophysical Research Communications, Academic Press Inc., Orlando, FL, vol. 313, No. 1, pp. 42-47, "Specific inhibition of hepatitis C virus replication by cyclosporin A", Jan. 2, 2004.

Bizollon T. et al., "Histological Benefit of Retreatment by Pegylated Interferon Alfa-2b and Ribavirin in Patients with Recurrent Hepatits C Virus Infection Posttransplantation", American Journal of Transplantation, vol. 7, pp. 448-453, (2007).

Cotler, Scott J. et al., "A Pilot Study of the Combination of Cyclosporin A and Interferon Alfacon-1 for the Treatment of Hepatitis C in Previous Nonresponder Patients", J Clin Gastroenterol , vol. 36 (4), pp. 352-355, (2003).

Shiffman (2004) Cleveland Clinic J. Med. 71:S13-S16.

Dasilva et al. (2002) J. Gastroenterol 37:732-36F.

Heathcote et al. (1998) Hepatology 27:4, pp. 1136-1143.

Package Insert for Intron A, Revision Jul. 2007.

International Search Report and written opinion for PCT/EP2005/007633, dated Oct. 19, 2005.

Inoue et al. "Hepatitis C, virus and cyclosporin A", Igaku no Ayumi, 193(12), pp. 951-954 (2000) Included are copies of the English abstract, the original document in Japanese, and an English translation of the original Japanese document.

U.S. Appl. No. 11/572,110: Non-Final Rejection mailed Aug. 6, 2008.

U.S. Appl. No. 11/572,110: Applicant Arguments/Remarks Made in an Amendment, Claims, Specification, Amemdment Request Reconsideration-After Non-Final Reject, submitted Nov. 5, 2008.

U.S. Appl. No. 11/572,110: Notice to the applicant regarding a non-compliant or non-responsive amendment mailed Dec. 5, 2008.

U.S. Appl. No. 11/572,110: Applicant Arguments/Remarks made in an Amendment, Claims, Specification, Amendment/Request Reconsideration after Non-Final rejection, filed Dec. 17, 2008.

U.S. Appl. No. 11/572,110: Final Rejection mailed Feb. 11, 2009.

U.S. Appl. No. 11/572,110: Arguments/Remarks Made in Amendment, Claims, Specification, Amendment Submitted/Entered May 11, 2009.

U.S. Appl. No. 11/572,110: Advisory Action mailed May 21, 2009.

U.S. Appl. No. 11/572,110: Request for Continued Examination filed May 29, 2009.

U.S. Appl. No. 11/572,110: Notice to the applicant regarding a non-complaint or non-responsive amendment mailed Jul. 10, 2009.

U.S. Appl. No. 11/572,110: Applicant Arguments/Remarks made in an Amendment, Amendment/Request Reconsideration after Non-Final rejection filed Jul. 28, 2009.

Flisiak et al , "The Cyclophilin Inhibitor Debio-025 Shows Potent Anti-Hepatitis C Effect in Patients Coinfected with Hepatitis C and Human Immunodeficiency Virus," Hepatology. pp. 817-826, (Mar. 2005).

Goto et al., "Evaluation of the anti-hepatitis C Virus effects of cyclophilin inhibitors., cyclosporine A, and NIM811," Biochemical and Biophysical Research Communications, vol. 343, pp. 879-884. (2006).

Ma et al., "NIM811, a Cyclophilin Inhibitor, Exhibits Potent In Vitro Activity against Hepatitis C Virus Alone or in Combination with Alpha Interferon," Antimicrobial Agents and Chemotherapy, vol. 50, No. 9, pp. 2976-2982, (Sep. 2008).

Paeshuyse et al., "The Non-Immunosuppressive Cyclosporin DEBI0-025 IS a Potent Inhibitor of Hepatitis C Virus Replication In Vitro," Hepatology, pp. 161-770, (Apr. 2006).

Kakumu et al, "Cyclosporine therapy affects aminotransferase activity but not hepatitis C virus RNA levels in chronic hepatitis C," Journal of Gastroenterology and Hepatology, vol. 12(1), pp. 62-65, (1997).

Watashi et al., "Cyclophilin B is a Functional Regulator of Hepatitis C Virus RNA Polymerase," Molecular Cell, vol. 19, pp. 111-122, (Jul. 1, 2005).

* cited by examiner

USE OF MODIFIED CYCLOSPORINS FOR THE TREATMENT OF HCV DISORDERS

CROSS-REFERENCE TO RELATED APPLICATIONS

This application is the National Stage of Application No. PCT/EP/2004/009804, filed on Sep. 2, 2004, which claim priority to GB0320638.0, filed Sep. 3, 2003, the contents of which are incorporated herein by reference in their entirety.

BACKGROUND OF THE DISCLOSURE

The present invention relates to a new use for non-immunosuppressive cyclosporins.

The cyclosporins comprise a class of structurally distinctive, cyclic, poly-N-methylated undecapeptides, commonly possessing pharmacological, in particular immunosuppressive, or anti-inflammatory activity. The first of the cyclosporins to be isolated was the naturally occurring fungal metabolite Ciclosporin or Cyclosporine, also known as cyclosporin A.

It is well established that cyclosporin A acts by interfering with the process of T cell activation by blocking transcription initiation of IL-2. Cyclosporin A has been shown to form a complex with a 17 kD cytosolic protein named as cyclophilin, that occurs in many cell types and has been shown to be identical to peptidyl-prolyl cis-trans isomerase, an enzyme involved in protein folding.

However, it was found that binding to cyclophilin is a necessary but not a sufficient criterion for immunosuppressive activity. The cyclosporin A/cyclophilin complex can also associate with the cellular protein named calcineurin (CN) which belongs to the phosphatase superfamiliy. This binding abrogates its phosphatase activity, resulting in silencing of transcription factor NF-AT. The inhibition of the CN/NF-AT pathway is the essential mechanism for cyclosporin A mediated immunosuppression.

Cyclosporins which bind strongly to cyclophilin but are not immunosuppressive have been identified. A cyclosporin is considered to be non-immunosuppressive when it has an activity in the Mixed Lymphocyte Reaction (MLR) of no more than 5%, preferably no more than 2%, that of cyclosporin A. The Mixed Lymphocyte Reaction is described by T. Meo in "Immunological Methods", L. Lefkovits and B. Peris, Eds., Academic Press, N.Y. pp. 227-239 (1979). Spleen cells (0.5×10⁶) from Balb/c mice (female, 8-10 weeks) are co-incubated for 5 days with 0.5×10⁶ irradiated (2000 rads) or mitomycin C treated spleen cells from CBA mice (female, 8-10 weeks). The irradiated allogeneic cells induce a proliferative response in the Balb c spleen cells which can be measured by labeled precursor Incorporation into the DNA. Since the stimulator cells are irradiated (or mitomycin C treated) they do not respond to the Balb/c cells with proliferation but do retain their antigenicity. The $IC_{50}$ found for the test compound in the MLR is compared with that found for cyclosporin A in a parallel experiment. In addition, non-immunosuppressive cyclosporins lack the capacity of inhibiting CN and the downstream NF-AT pathway.

EP 0 484 281 A1 discloses the use of non-immunosuppressive cyclosporins in the treatment of AIDS or AIDS-related disorders.

BRIEF SUMMARY OF THE DISCLOSURE

It has now surprisingly been found that non-immunosuppressive cyclosporins which bind to cyclophilin have an inhibitory effect on Hepatitis C virus (HCV).

Persistent infection by HCV, which has been identified as the major causative agent of non-A, non-B hepatitis has been considered closely related to liver diseases such as chronic hepatitis, liver cirrhosis or hepatocellular carcinoma. The development of these liver diseases is a major public health problem. Effective anti-HCV therapy is restricted to therapy with interferon or a combination of interferon and ribavirin. However, since the virus is not eliminated from about a half of the HCV patients treated with these known agents, there is still a strong need for alternative anti-HCV agents.

Accordingly, the present invention provides the use of a non-immunosuppressive cyclophilin-binding cyclosporin in the prevention or treatment of Hepatitis C infections or HCV induced disorders.

Hepatitis C infections or HCV induced disorders are e.g. chronic hepatitis, liver cirrhosis or liver cancer, e.g. hepatocellular carcinoma. The non-immunosuppressive cyclophilin-binding cyclosporins may also be used for example as a prophylactic treatment of neonates born to HCV infected mothers or of healthcare workers exposed to the virus, or of transplant recipients, e.g. organ or tissue transplant recipients, e.g. liver transplant, to eliminate possible recurrent HCV infection after transplantation.

A cyclosporin is considered as binding to cyclophilin if it binds to human recombinant cyclophilin at least one fifth as well as does cyclosporin A in the competitive ELISA test described by Quesniaux in Eur. J. Immunol. 1987 17 1359-1365. In this test, the cyclosporin to be tested is added during the incubation of cyclophilin with coated BSA-cyclosporin A and the concentration required to give a 50% inhibition of the control reaction without competitor is calculated ($IC_{50}$). The results are expressed as the Binding Ratio (BR), which is the log to the base 10 of the ratio of the $IC_{50}$ of the test compound and the $IC_{50}$ in a simultaneous test of cyclosporin A itself. Thus a BR of 1.0 indicates that the test compound binds human cyclophilin one factor of ten less well than does cyclosporin A, and a negative value indicates binding stronger than that of cyclosporin A. The cyclosporins active against HCV have a BR lower than 0.7, preferably equal to or lower than zero.

Examples of non immunosuppressive cyclophilin-binding cyclosporins include e.g. compounds of Formula I $$\boxed{\text{W-X-R-Y-Z-Q-Ala-T}_1\text{-T}_2\text{-T}_3\text{-MeVal}} \quad \text{I}$$
$$\phantom{\boxed{\;\;}}1\;\;2\;\;3\;\;4\;\;5\;\;6\;\;7\;\;8\;\;9\;\;10\;\;11$$

wherein

W is MeBmt, dihydro-MeBmt, 8'-hydroxy-MeBmt or O-acetyl-MeBmt[1];

X is αAbu, Val, Thr, Nva or 0-methyl threonine (MeOThr);

R is Pro, Sar, (D)-MeSer, (D)-MeAla, or (D)-MeSer (Oacetyl);

Y is MeLeu, thioMeLeu, γ-hydroxy-MeLeu, MeIle, MeVal, MeThr, MeAla, MeaIle or MeaThr; N-ethylVal, N-ethylIle, N-ethylThr, N-ethylPhe, N-ethylTyr or N-ethylThr(Oacetyl)

Z is Val, Leu, MeVal or MeLeu,

Q is MeLeu, γ-hydroxy-MeLeu, MeAla or Pro, $T_1$ is (D) Ala or Lys, $T_2$ is MeLeu or γ-hydroxy-MeLeu, and $T_3$ is MeLeu or MeAla.

Preferred compounds of formula I are e.g. compounds of formula Ia

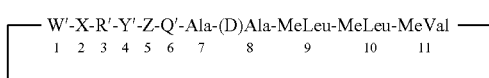

in which W' is MeBmt, dihydro-MeBmt or 8'-hydroxy-MeBmt;
X is αAbu, Val, Thr, Nva or 0-methyl threonine (MeOThr);
R' is Sar, (D)-MeSer, (D)-MeAla, or (D)-MeSer(Oacetyl);
Y' is MeLeu, γ-hydroxy-MeLeu, MeIle, MeVal, MeThr, MeAla, MeaIle or MeaThr; N-ethylVal, N-ethylIle, N-ethylThr, N-ethylPhe, N-ethylTyr or N-ethylThr (Oacetyl)
Z is Val, Leu, MeVal or MeLeu; and
Q' is MeLeu, γ-hydroxy-MeLeu or MeAla.

The groups W', X, Y', Z, Q' and R' have, independently, the following preferred significances:
W' is preferably W" where W" is MeBmt or dihydro-MeBmt;
X is preferably X' where X' is αAbu or Nva, more preferably X" where X" is αAbu;
R' is preferably R" where R" is Sar;
Y' is preferably Y" where Y" is γ-hydroxy-MeLeu, MeVal, MeThr, MeIle, N-ethylIle or N-ethylVal;
Z is preferably Z' where Z' is Val or MeVal; and
Q' is preferably Q" where Q" is MeLeu;

A preferred group of Compounds of formula Ia are those in which W' is W", X is X', Y' is Y", Z is Z', Q' is Q" and R' is R".
Examples of preferred compounds of Formula Ia are e.g.:
a) [dihydro-MeBmt]$^1$-[γ-hydroxy-MeLeu]$^4$-Ciclosporin; BR*=0.1; IR<1%
b) [MeVal]$^4$-Ciclosporin; BR=0.1; IR<1%
c) [MeIle]$^4$-Ciclosporin; BR=–0.2; IR<1%
d) [MeThr]$^4$-Ciclosporin;
e) [γ-hydroxy-MeLeu]$^4$-Ciclosporin; BR=0.4; IR<1%
f) [Ethyl-Ile]$^4$-Ciclosporin; BR=0.1; IR<2%
g) [Ethyl-Val]$^4$-Ciclosporin; BR=0; IR<2%
h) [Nva]$^2$-[γ-hydroxy-MeLeu]$^4$-Ciclosporin;
i) [γ-hydroxy-MeLeu]$^4$-[γ-hydroxy-MeLeu]6-Ciclosporin;
j) [MeVal]$^5$-Ciclosporin; BR=0.4; IR=5.3%
k) [MeOThr]$^2$-[(D)MeAla]$^3$-[MeVal]$^5$-Ciclosporin;
j) [8'-hydroxy-MeBmt]$^1$-Ciclosporin; BR=0.35; IR=1.8%
k) [MeAla]$^6$-Ciclosporin; BR=–0.4; IR=3.2
l) [γ-hydroxy-MeLeu]$^9$-Ciclosporin; BR=0.15; IR=2.9

IR=Immunosuppressive Ratio, expressed as a percentage of the activity relative to Cyclosporin A.

Further examples of non-immunosuppressive cyclosporins are the compounds disclosed in WO 98/28330, WO 98/28329 and WO 98/28328, the contents thereof being incorporated herein by reference, e.g. compounds of formula II

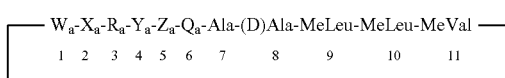

wherein
$W_a$ is

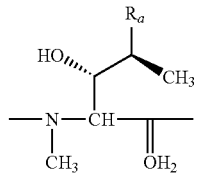

wherein $R_a$ is a residue of formula Ic or Id

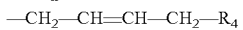

or

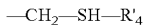

in which $R_4$ is $C_{1-4}$alkylthio, amino$C_{1-4}$alkylthio, $C_{1-4}$alkylamino$C_{1-4}$-alkylthio, di$C_{1-4}$alkylamino-$C_{1-4}$alkylthio, pyrimidinylthio, thiazolylthio, N—$C_{1-4}$alkylimidazolylthio, hydroxy$C_{1-4}$alkylphenylthio, hydroxy$C_{1-4}$alkylphenoxy, nitrophenylamino or 2-oxopyrimidin-1-yl, and R'$_4$ is $C_{1-4}$alkyl,
$X_a$ is Abu;
$R_a$ is —NMe-CH($R_b$)—CO— wherein $R_b$ is H or —S-Alk-$R_0$ in which Alk-$R_0$ is methyl; or Alk is straight or branched $C_{2-6}$alkylene or $C_{3-6}$cycloalkylene and $R_0$ is H; OH; COOH; $C_{2-5}$alkoxy-carbonyl; $NR_1R_2$ in which each of $R_1$ and $R_2$, independently, is selected from H, $C_{1-4}$alkyl, $C_{2-4}$alkenyl, $C_{3-6}$cycloalkyl and phenyl each optionally substituted by halogen, $C_{1-4}$alkoxy, $C_{2-5}$alkoxycarbonyl, amino, $C_{1-4}$alkylamino and/or di$C_{1-4}$alkyl-amino, and benzyl and a heterocyclic radical, said benzyl and heterocyclic radicals being saturated or unsaturated and containing 5 or 6 ring members and 1 to 3 heteroatoms, or $R_1$ and $R_2$ form, together with the nitrogen atom to which they are attached, a 4- to 6 membered heterocycle which may contain another heteroatom chosen from nitrogen, oxygen and sulphur, and which is optionally substituted by $C_{1-4}$alkyl, phenyl or benzyl; or each of $R_1$ and $R_2$, independently, is a radical of formula Ib

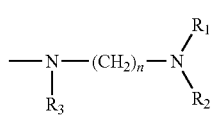

in which $R_1$ and $R_2$ are as defined above, $R_3$ is H or $C_{1-4}$alkyl and n is an integer ranging from 2 to 4;
$Y_a$ is MeLeu or γ-hydroxy-MeLeu;
$Z_a$ is Val; and
$Q_a$ is MeLeu,
with the proviso that $R_b$ is not H when $Y_a$ is MeLeu, or a pharmaceutically acceptable salt thereof.

In the formula II, when $R_1$ and/or $R_2$ is a heterocyclic residue, it may be pyridyl, tetrahydro-pyridyl, piperidyl, imidazolyl, oxazolyl or thiazolyl. When $R_1$ and $R_2$ form a heterocyclic residue with the nitrogen atom to which they are attached, by way of example, the heterocyclic residue may be chosen from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl (for example 4-methyltetrahydropyridyl) or phenyltetrahydropyridyl (for example 4-phenyltetrahydropyridyl).

The Compounds of formula I, Ia or II may be obtained in a variety of ways, which may be classified as:
1) Fermentation
2) Biotransformation
3) Derivatisation
4) Partial Synthesis
5) Total Synthesis as disclosed e.g. in EP 0 484 281 A1, WO 00/01715, WO 98/28330, WO 98/28329 or WO 98/28328 the contents thereof being incorporated herein by reference.

In a series of further specific or alternative embodiments, the present invention also provides:

1.1 A method for preventing or treating Hepatitis C infections or HCV induced disorders in a subject in need thereof, comprising administering to said subject a therapeutically effective amount of a non-immunosuppressive cyclophilin-binding cyclosporin, e.g. a compound of formula I, Ia or II.

According to the invention, the non-immunosuppressive cyclophilin-binding cyclosporine may be administered in an amount effective to alleviate or eliminate one or more of the signs or symptoms of hepatitis C, for example, effective to lower the HCV-RNA measured in a serum sample of a subject.

1.2 A method for inhibiting HCV replication in a medium, comprising applying to this medium an effective amount of a non-immunosuppressive cyclophilin-binding cyclosporin, e.g. a compound of formula I, Ia or II.

1.3 A method for inhibiting HCV replication in a patient in need thereof, comprising administering to this subject a therapeutically effective amount of a non-immunosuppressive cyclophilin-binding cyclosporin, e.g. a compound of formula I, Ia or II.

1.4 A method for preventing the recurrence of HCV infection in a transplant recipient in need thereof, comprising administering to said recipient a therapeutically effective amount of a non-immunosuppressive cyclophilin-binding cyclosporin, e.g. a compound of formula I, Ia or II.

2. Use of a non-immunosuppressive cyclophilin-binding cyclosporin, e.g. a compound of formula I, Ia or II, in the preparation of a pharmaceutical composition for use in any method as defined above.

3. A pharmaceutical composition for use in any method as defined above, comprising a non-immunosuppressive cyclophilin-binding cyclosporin, e.g. a compound of formula I, Ia or II, together with one or more pharmaceutically acceptable diluents or carriers therefor.

DETAILED DESCRIPTION OF THE DISCLOSURE

Figure 1:
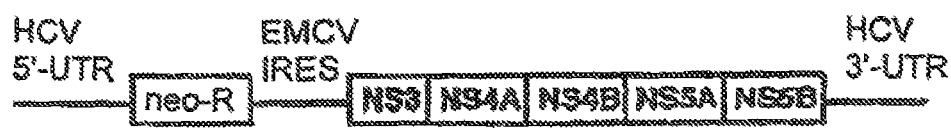
FIG. 1 shows a diagram of the HCV subgenomic replicon used in the disclosed experiments.

Utility of the non-immunosuppressive cyclophilin-binding cyclosporins (hereinafter "cyclosporins of the invention") in treating diseases and conditions as hereinabove specified may be demonstrated in standard animal or clinical tests, e.g. in accordance with the methods described hereinafter.

A. In Vitro

Cell culture: Huh-7 and MH-14 cells, HCV replicon cells, are cultured in Dulbecco's modified Eagle's medium (DMEM) with 10% fetal bovine serum (FBS). PH5CH8 cells are cultured in a 1:1 mixture of DMEM and F12 medium supplemented with 100 ng/ml of epidermal growth factor, 10 µu/ml of insulin, 0.36 µg/ml of hydrocortisone, 5 µg/ml of transferrin, 5 µg/ml of linoleic acid, 20 ng/ml of selenium, 4 µg/ml of glucagon, 10 ng/ml of prolactin, 10 µg/ml of gentamicin, 200 µg/ml of kanamycin, and 2% FBS.

Immunoblot analysis: Immunoblot analysis is performed as described by K. Watashi et al., Virology 2001, 286, 391-402. The primary antibodies used in this experiment are anti-NS5A, anti-NS5B, and anti-β-actin (Sigma) antibodies.

Indirect immunofluorescence analysis: Indirect immunofluorescence analysis is performed as described by K. Watashi, supra. The primary antibodies used in this experiment are anti-NS5A and anti-PDI (StressGen) antibodies.

Reverse Transcription (RT)-polymerase Chain Reaction (PCR) Analysis

Total RNA of cultured cells is isolated with Sepasol-RNA I Super (nacalai tesque) as recommended by the manufacturer. RT-PCR analysis is performed using a one step RNA PCR kit (Takara) according to the manufacturer's directions. The primers used for detection of mRNAs for 2',5'-oligoadenylate synthetase and double strand RNA-dependent protein kinase are 5'-CCGTGAAGTTTGAGGTCCAG-3', 5'-GAC-TAATTCCAAGACCGTCCG-3' and 5'-TGGC-CGCTAAACTTGCATATC-3', 5'-GCGAGTGTGCTGGT-CACTAAAG-3', respectively.

Northern Blot Analysis: Nothern blot analysis is performed as described by H. Kishine et al., Biochem. Biophys. Res. Commun., 2002, 47, 119-125. The probe complementary to the NS5B sequence used in this experiment is described by H. Kishine, supra.

Real Time RT-PCR Analysis: The 5'-UTR of HCV genome RNA is quantified using the ABI PRISM 7700 sequence detector (AppliedBiosystems) as described by T. Takeuchi et al., Gastroenterology, 1999, 116, 636-642. The forward and reverse primers used in this experiment are 5'-CGG-GAGAGCCATAGTGG-3' and 5'-AGTACCACAAGGC-CTTTCG-3', respectively. The fluorogenic probe is 5'-CT-GCGGAACCGGTGAGTACAC-3'. As an internal control, ribosomal RNA is also quantified using TaqMan Ribosomal RNA Control Reagents (Applied Biosystems).

In Vitro HCV Infection Experiment: The in vitro HCV infection experiment is performed essentially as described by N. Kato et al., Jpn. J. Cancer Res. 1996, 87, 787-792 and M. Ikada et al., Virus Res., 1998, 56, 157-167. PH5CH8 cells ($1 \times 10^5$) are infected with the plasma 1B-2 (equivalent to $10^4$ to $10^5$ HCV RNA copies), which is prepared from an HCV-positive blood donor. At 24 h post-inoculation, the cells are washed three times with phosphate-buffered saline (PBS) and maintained with fresh medium.

Transfection and Reporter Assay: Transfection into MH-14 and H9 cells is performed using FuGENE 6 (Roche) and Lipofectamine 2000 transfection reagent (Invitrogen), respectively, according to the manufacturer's protocol. The reporter assay is performed as described by K. Watashi, supra. The reporter plasmids used in this study are pNFAT-Luc, pAP1-Luc, pNFKB-Luc (PathDetect Reporter System; Stratagene), and pRL-TK (Dual-luciferase reporter assay system; Promega).

The effect of various cyclosporins of the invention on the replication of the HCV genome using MH-14 cells, in which the HCV subgenomic replicon as shown in FIG. 1A is autonomously replicated. Treatment with a cyclosporin of the invention, e.g. [MeIle]$^4$-ciclosporin, e.g. at 1 μg/ml, as well as 100 U/ml IFNα which is used as a positive control for 7 days decreases the amount of HCV NS5A and NS5B proteins to levels undetectable by immunoblot analysis. Indirect immunofluorescence analysis showed that NS5A protein production is reduced in all the cells treated with 1 μg/ml cyclosporin of the invention, while the level of protein disulfide isomerase (PDI), which is an endoplasmic reticulum marker, as an internal control is not altered under this condition. The cyclosporins of the invention decrease in this assay HCV protein expression in HCV replicon cells.

Replicon RNA is analyzed in MH-14 cells treated with or without a cyclosporin of the invention or IFNα for 7 days by northern blot analysis. Treatment with e.g. 1 μg/ml cyclosporin of the invention, e.g. [MeIle]$^4$-ciclosporin, decreases the amount of replicon RNA to an undetectable level. Treatment with 100 U/ml IFNα produces a similar effect. In addition the titer is gradually decreased and the level of HCV RNA is reduced to about 1/400 of the original on the 7$^{th}$ day. In the case of a co-treatment with IFNα, a further reduction at any time point examined (3th, 5$^{th}$ and 7$^{th}$ day) compared with the single treatment with either the cyclosporin or IFNα: the replicon RNA level in MH-14 cells treated with both the cyclosporin and IFNα for 7 days is significantly decreased over that in the cells treated with IFNα alone.

Furthermore, PH5CH8 cells (non-neoplastic hepatocyte cell line) are treated with HCV-positive plasma and subsequently the HCV RNA genome titer at various time-points post-inoculation is quantified by real time RT-PCR analysis. While the HCV RNA genome titer on the 5$^{th}$ day post-inoculation in the cells is increased about 10-fold compared with that on the 1$^{st}$ day, a significant increase of the HCV RNA genome titer at these time points was not observed in the cells treated continuously with a cyclosporin of the invention, e.g. [MeIle]$^4$-ciclosporin, or IFNα. The cyclosporins of the invention inhibit the replication of HCV infected cultured hepatocytes.

Figure 2:
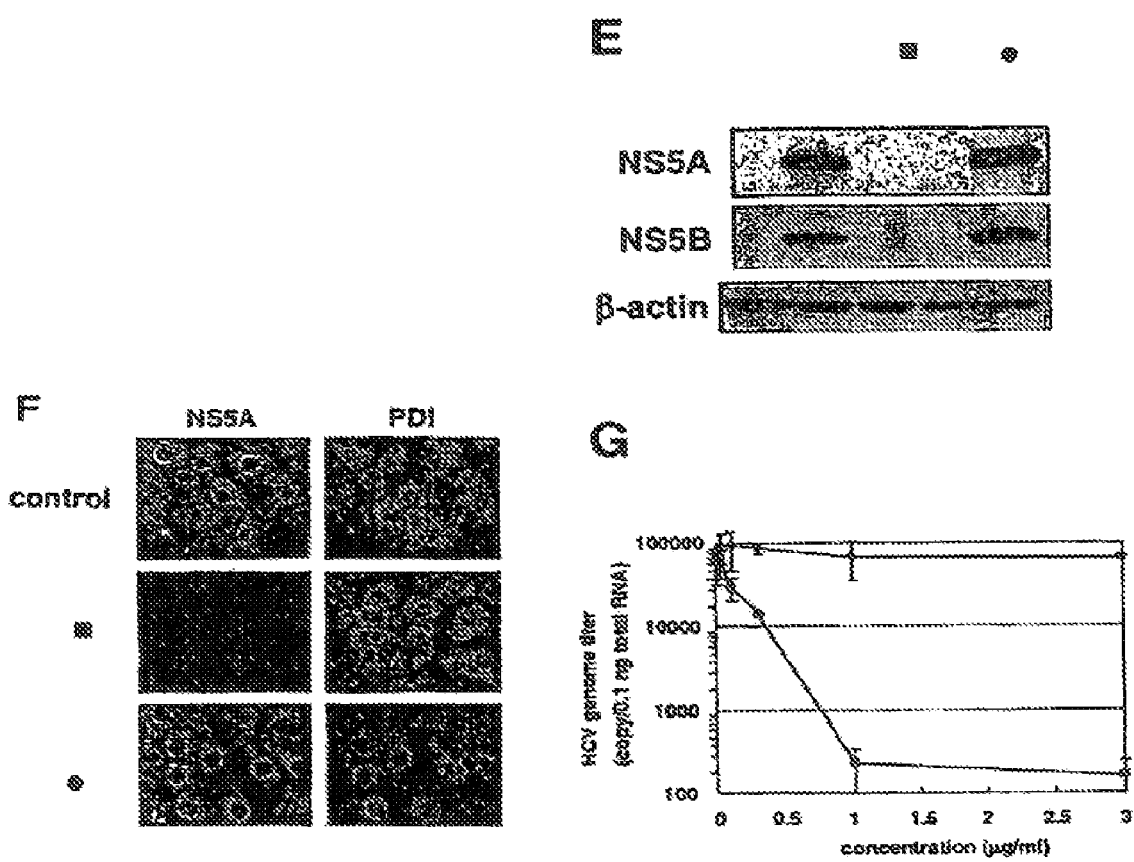
FIG. 2 shows the results of experiments using MH-14 cells containing an HCV subgenomic replicon and testing the activity of a non-immunosuppressive cyclophilin-binding cyclosporin (e.g., 6-[[R-(E)]-6,7-Didehydro-N,4-dimethyl-3-oxo-L-2-aminooctanoic acid]-7-L-valine-cyclosporin A). E) Immunoblot analysis; F) immunofluorescence analysis; G) real time PCR. Controsl in E and F (first row), no treatment CysA in E. 1 µg/ml; [MeIle]$^4$-cyclosporin in E (■) and F (■), 1 µg/ml; the noncyclophilin binding cyclosporin in E (●)and F (●), 1 µg/ml.

Results are shown in FIGS. 2E, 2F and 2G: immunoblot analysis (2E), indirect immunofluorescence analysis (2F) and real time RT-PCR analysis (2G) is performed using MH-14 cells treated with [MeIle]$^4$-Ciclosporin (■) or an non cyclophilin binding cyclosporin (●), e.g. 6-[[R-(E)]-6,7-Didehydro-N,4-dimethyl-3-oxo-L-2-aminooctanoic acid]-7-L-valine-cyclosporin A. Control in 2E and 2F (1$^{st}$ row), no treatment; CysA in 2E, 1 μg/ml; [MeIle]$^4$-Ciclosporin in 2E (■) and 2F (■), 1 μg/ml; the non cyclophilin binding cyclosporin in 2E (●) and 2F (●), 1 μg/ml.

B. Clinical Trial

A total of 15 patients with chronic Hepatitis C infection are enrolled in a study of 2 weeks. Each patient receives a cyclosporine of the invention, e.g. [MeIle]$^4$-ciclosporin, at a dose of 7 to 15 mg/kg p.o. The serum levels of Hepatitis C antigens are determined at day 0 and day 14 in each patient.

A person suffering from hepatitis C infection, in particular chronic HCV infection, may exhibit one or more of the following signs or symptoms: (a) elevated ALT, (b) positive test for anti-HCV antibodies, (c) presence of HCV as demonstrated by a positive test for HCV-RNA, (d) clinical stigmata of chronic liver disease, (e) hepatocellular damage. Such criteria may not only be used to diagnose Hepatitis C, but can be used to evaluate a patient's response to drug treatment.

Elevated serum alanine aminotransferase (ALT) and aspartate aminotransferase (AST) are known to occur in uncontrolled Hepatitis C, and a complete response to treatment is generally defined as the normalization of these serum enzymes, particularly ALT (Davis et al., 1989, New Eng. J. Med. 321:1501-1506). ALT is an enzyme released when liver cells are destroyed and is symptomatic of HCV infection.

In order to follow the course of HCV replication in subjects in response to drug treatment, HCV RNA may be measured in serum samples by, for example, a nested polymerase chain reaction assay that uses two sets of primers derived from the N53 and N54 non-structural gene regions of the HCV genome. Farci et al., 1991, New Eng. J. Med. 325:98-104. Ulrich et al., 1990, J. Clin. Invest., 86:1609-1614.

Histological examination of liver biopsy samples may be used as a second criteria for evaluation. See, e.g., Knodell et al., 1981, Hepatology 1:431-435, whose Histological Activity Index (portal inflammation, piecemeal or bridging necrosis, lobular injury and fibrosis) provides a scoring method for disease activity.

Daily dosages required in practicing the method of the present invention will vary depending upon, for example, the non-immunosuppressive cyclophilin-binding cyclosporin employed, the host, the mode of administration, the severity of the condition to be treated. A preferred daily dosage range is about from 1 to 50 mg/kg per day as a single dose or in divided doses. Suitable daily dosages for patients are on the order of from e.g. 1 to 20 mg/kg p.o or i.v. Suitable unit dosage forms for oral administration comprise from ca. 0.25 to 10 mg/kg active ingredient, e.g. [MeIle]$^4$-ciclosporin, together with one or more pharmaceutically acceptable diluents or carriers therefor.

The cyclosporins of the invention may be administered by any conventional route, in particular enterally, e.g. orally, for example in the form of solutions for drinking, tablets or capsules or parenterally, for example in the form of injectable solutions or suspensions. Preferred pharmaceutical compositions may be e.g. those based on microemulsions as described in UK 2,222,770 A.

The cyclosporins of the invention may be administered as the sole ingredient or together with other drugs, e.g. a drug which has anti-HCV activities, e.g. an interferon, e.g. interferon-α-2a or interferon-α-2b, e.g. Intron$^R$ A, Roferon$^R$, Avonex$^R$, Rebif$^R$ or Betaferon$^R$, or an interferon conjugated to a water soluble polymer or to human albumin, e.g. albuferon, an anti-viral agent, e.g. ribavirin, lamivudine, NV08 or NM283, an inhibitor of the HCV encoded factors like the NS3/4A protease, the helicase or RNA polymerase or a prodrug of such an inhibitor, an anti-fibrotic agent, e.g. a N-phenyl-2-pyrimidine-amine derivative, e.g. imatinib, an immune modulating agent, e.g. mycophenolic acid, a salt or a prodrug thereof, e.g. sodium mycophenolate or mycophenolate mofetil, or a S1P receptor agonist, e.g. FTY720 or an analogue thereof optionally phosphorylated, e.g. as disclosed in EP627406A1, EP778263A1, EP1002792A1, WO02/18395, WO02/76995, WO 02/06268, JP2002316985, WO03/29184, WO03/29205, WO03/62252 and WO03/62248.

Conjugates of interferon to a water-soluble polymer are meant to include especially conjugates to polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917, 888, European Patent Application No. 0 236 987, European Patent Application No. 0 510 356 and International Application Publication No. WO 95/13090. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

Especially preferred conjugates of interferon are pegylated alfa-interferons, for example pegylated interferon-α-2a, pegylated interferon-α-2b; pegylated consensus interferon or pegylated purified interferon-α product. Pegylated interferon-α-2a is described e.g. in European Patent 593,868 and commercially available e. g. under the tradename PEGASYS® (Hoffmann-La Roche). Pegylated interferon-α-2b is described, e.g. in European Patent 975,369 and commercially available e.g. under the tradename PEG-INTRON A® (Schering Plough). Pegylated consensus interferon is described in WO 96/11953. The preferred pegylated α-interferons are pegylated interferon-α-2a and pegylated interferon-α-2b. Also preferred is pegylated consensus interferon.

Daily dosages with respect to the co-agent used will vary depending upon, for example, the compound employed, the host, the mode of administration and the severity of the condition to be treated. For example, lamivudine may be administered at a daily dosage of 100 mg. The pegylated interferon may be administered parenterally one to three times per week, preferably once a week, at a total weekly dose ranging from 2 to 10 million IU, more preferable 5 to 10 million IU, most preferable 8 to 10 million IU.

In accordance with the foregoing the present invention provides in a yet further aspect:

4. A pharmaceutical combination comprising a) a first agent which is a non-immunosuppressive cyclophilin-binding cyclosporin, e.g. a compound of formula I, Ia or II, and b) a co-agent, e.g. a second drug agent as defined above, e.g. for use in any method as defined above.

5. A method as defined above comprising co-administration, e.g. concomitantly or in sequence, of a therapeutically effective amount of a non-immunosuppressive cyclophilin-binding cyclosporin, e.g. a compound of formula I, Ia or II, and a co-agent, e.g. a second drug agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The administration of a pharmaceutical combination of the invention results in a beneficial effect, e.g. a synergistic therapeutic effect, compared to a monotherapy applying only one of its pharmaceutically active ingredients. A preferred synergistic combination is a combination of a non-immunosuppressive cyclophilin-binding cyclosporin with an interferon, optionally conjugated to a polymer.

A further preferred combination is a combination of a non-immunosuppressive cyclophilin-binding cyclosporin with mycophenolic acid, a salt or a prodrug thereof, or with a S1P receptor agonist, e.g. FTY720.

[MeIle]⁴-ciclosporin or [MeVal]⁴-Ciclosporin is a preferred non-immunosuppressive cyclophilin-binding cyclosporin for use according to the invention.

The invention claimed is:

1. A method for inhibiting HCV replication in a medium, comprising applying to said medium an effective amount of a cyclosporin according to formula Ia:

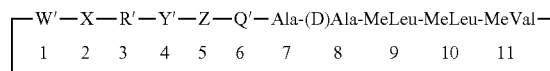

in which

W' is MeBmt, dihydro-MeBmt or 8'-hydroxy-MeBmt;

X is αAbu, Val, Thr, Nva, or O-methyl threonine (Me-O-Thr);

R' is Sar, (D)-MeSer, (D)-MeAla, or (D)-MeSer(O-Acetyl);

Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl)

Z is Val, Leu, MeVal or MeLeu; and

Q' is MeLeu, γ-hydroxy-MeLeu or MeAla, or a pharmaceutically acceptable salt thereof, wherein the cyclosporin (i) binds to human recombinant cyclophilin with a binding ratio (BR) of less than 0.7, BR being the log to base 10 of the ratio of the IC₅₀ of the cyclosporin to the IC₅₀ of cyclosporin A as measured in a competitive ELISA test; and (ii) has an activity in the Mixed Lymphocyte Reaction (MLR) of not more than 5% that of cyclosporin A.

2. A method for inhibiting HCV replication, comprising administering to a subject in need thereof a therapeutically effective amount of a cyclosporin according to formula Ia:

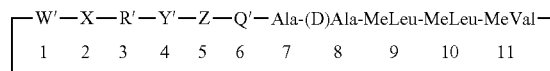

in which

W' is MeBmt, dihydro-MeBmt or 8'-hydroxy-MeBmt;

X is αAbu, Val, Thr, Nva, or O-methyl threonine (Me-O-Thr);

R' is Sar, (D)-MeSer, (D)-MeAla, or (D)-MeSer(O-Acetyl);

Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl)

Z is Val, Leu, MeVal or MeLeu; and

Q' is MeLeu, γ-hydroxy-MeLeu or MeAla, or a pharmaceutically acceptable salt thereof, wherein the cyclosporin (i) binds to human recombinant cyclophilin with a binding ratio (BR) of less than 0.7, BR being the log to base 10 of the ratio of the IC₅₀ of the cyclosporin to the IC₅₀ of cyclosporin A as measured in a competitive ELISA test; and (ii) has an activity in the Mixed Lymphocyte Reaction (MLR) of not more than 5% that of cyclosporin A.

3. A method for treating the recurrence of HCV infection in a transplant recipient, comprising administering'to a transplant recipient in need thereof a therapeutically effective amount of a cyclosporin according to formula Ia:

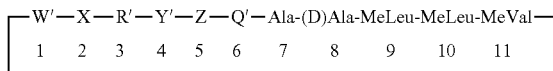

in which
W' is MeBmt, dihydro-MeBmt or 8'-hydroxy-MeBmt;
X is αAbu, Val, Thr, Nva, or O-methyl threonine (Me-O-Thr);
R' is Sar, (D)-MeSer, (D)-MeAla, or (D)-MeSer(O-Acetyl);
Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl)
Z is Val, Leu, MeVal or MeLeu; and
Q' is MeLeu, γ-hydroxy-MeLeu or MeAla, or a pharmaceutically acceptable salt thereof, wherein the cyclosporin
 (i) binds to human recombinant cyclophilin with a binding ratio (BR) of less than 0.7, BR being the log to base 10 of the ratio of the IC$_{50}$ of the cyclosporin to the IC$_{50}$ of cyclosporin A as measured in a competitive ELISA test; and
 (ii) has an activity in the Mixed Lymphocyte Reaction (MLR) of not more than 5% that of cyclosporin A,
 and wherein said cyclosporin treats the recurrence of HCV infection by inhibiting Hepatitis C viral replication in said recipient.

4. The method according to claim 2, further comprising co-administering concomitantly or in sequence a therapeutically effective amount of a co-agent selected from the group consisting of an agent having anti-HCV properties, FTY720, an anti-fibrotic agent, an immune modulating agent and a S1P receptor agonist.

5. The method of claim 1, wherein said cyclosporin according to formula Ia or a pharmaceutically acceptable salt thereof is administered as part of a pharmaceutical composition.

6. The method of claim 2, wherein said cyclosporin according to formula Ia or a pharmaceutically acceptable salt thereof is administered as part of a pharmaceutical composition.

7. The method of claim 3, wherein said cyclosporin according to formula Ia or a pharmaceutically acceptable salt thereof is administered as part of a pharmaceutical composition.

8. The method of claim 6, further comprising administering a co-agent having anti-HCV properties.

9. A method for lowering the HCV-RNA measured in a serum sample from a subject, comprising administering to a subject in need thereof a therapeutically effective amount of a cyclosporin according to formula Ia:

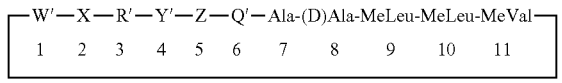

in which
W' is MeBmt, dihydro-MeBmt or 8'-hydroxy-MeBmt;
X is αaAbu, Val, Thr, Nva, or O-methyl threonine (Me-O-Thr);
R' is Sar, (D)-MeSer, (D)-MeAla, or (D)-MeSer(O-Acetyl);
Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl)
Z is Val, Leu, MeVal or MeLeu; and
Q' is MeLeu, γ-hydroxy-MeLeu or MeAla, or a pharmaceutically acceptable salt thereof, wherein the cyclosporin
 (i) binds to human recombinant cyclophilin with a binding ratio (BR) of less than 0.7. BR being the log to base 10 of the ratio of the IC$_{50}$ of the cyclosporin to the IC$_{50}$ of cyclosporin A as measured in a competitive ELISA test; and
 (ii) has an activity in the Mixed Lymphocyte Reaction (MLR) of not more than 5% that of cyclosporin A.

10. A method for the treatment of a Hepatitis C infection, comprising administering to a subject in need thereof a cyclosporin according to formula Ia:

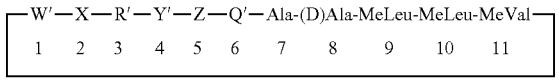

in which
W' is MeBmt, dihydro-MeBmt or 8'-hydroxy-MeBmt;
X is αAbu, Val, Thr, Nva, or O-methyl threonine (Me-O-Thr);
R' is Sar, (D)-MeSer, (D)-MeAla, or (D)-MeSer(O-Acetyl);
Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl)
Z is Val, Leu, MeVal or MeLeu; and
Q' is MeLeu, γ-hydroxy-MeLeu or MeAla, or a pharmaceutically acceptable salt thereof, wherein the cyclosporin
 (i) binds to human recombinant cyclophilin with a binding ratio (BR) of less than 0.7. BR being the log to base 10 of the ratio of the IC$_{50}$ of the cyclosporin to the IC$_{50}$ of cyclosporin A as measured in a competitive ELISA test: and
 (ii) has an activity in the Mixed Lymphocyte Reaction (MLR) of not more than 5% that of cyclosporin A.
 and wherein said cyclosporin treats the Hepatitis C infection by inhibiting Hepatitis C viral replication in said subject.

11. A method of inhibiting Hepatitis C replication in a subject by binding cyclophilin in said subject in need thereof with a cyclosporin, comprising administering to the subject a therapeutically effective amount a cyclosporin of formula Ia:

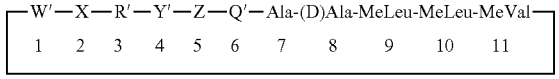

in which
W' is MeBmt, dihydro-MeBmt or 8'-hydroxy-MeBmt;
X is αAbu, Val, Thr, Nva, or O-methyl threonine (Me-O-Thr);

R' is Sar, (D)-MeSer, (D)-MeAla, or (D)-MeSer(O-Acetyl);

Y' is MeLeu, γ-hydroxy-MeLeu, MeVal, MeIle, MeThr, MeAla; MeaIle or MeaThr; N-ethylVal, N-ethylIle, N-ethylThr, N-ethylPhe, N-ethylTyr or N-ethylThr(O-Acetyl);

Z is Val, Leu, MeVal or MeLeu; and

Q' is MeLeu, γ-hydroxy-MeLeu or MeAla, or a pharmaceutically acceptable salt thereof, wherein the cyclosporin (i) binds to human recombinant cyclophilin with a binding ratio (BR) of less than 0.7. BR being the log to base 10 of the ratio of the $IC_{50}$ of the cyclosporin to the $IC_{50}$ of cyclosporin A as measured in a competitive ELISA test; and (ii) has an activity in the Mixed Lymphocyte Reaction (MLR) of not more than 5% that of cyclosporin A.

12. The method according to claim 11, further comprising co-administering concomitantly or in sequence a therapeutically effective amount of a co-agent selected from the group consisting of an agent having anti-HCV properties, FTY720, an anti-fibrotic agent, an immune modulating agent and a S1P receptor agonist.

13. The method of claim 11, wherein said cyclosporin according to formula Ia or a pharmaceutically acceptable salt thereof is administered as part of a pharmaceutical composition.

* * * * *